US010338049B2

United States Patent
Schelch et al.

(10) Patent No.: US 10,338,049 B2
(45) Date of Patent: Jul. 2, 2019

(54) ELECTROCHEMICAL METHOD AND DEVICE FOR DETERMINING THE CONTENT OF DOC AND/OR TOC AND/OR IC IN AN AQUEOUS SAMPLE

(71) Applicant: PRO AQUA DIAMANTELEKTRODEN PRODUKTION GMBH & CO KG, Niklasdorf (AT)

(72) Inventors: Michael Schelch, Oberaich (AT); Wolfgang Staber, Bruck an der Mur (AT); Robert Hermann, Oberaich (AT); Wolfgang Wesner, Vienna (AT)

(73) Assignee: PRO AQUA DIAMANTELEKTRODEN PRODUKTION GMBH & CO KG, Niklasdorf (AT)

( * ) Notice: Subject to any disclaimer, the term of this patent is extended or adjusted under 35 U.S.C. 154(b) by 560 days.

(21) Appl. No.: 15/033,091

(22) PCT Filed: Oct. 21, 2014

(86) PCT No.: PCT/EP2014/072510
§ 371 (c)(1),
(2) Date: Apr. 28, 2016

(87) PCT Pub. No.: WO2015/062911
PCT Pub. Date: May 7, 2015

(65) Prior Publication Data
US 2016/0258921 A1 Sep. 8, 2016

(30) Foreign Application Priority Data
Oct. 30, 2013 (AT) .............................. A 50707/2013

(51) Int. Cl.
*G01N 27/30* (2006.01)
*G01N 33/18* (2006.01)
*G01N 27/416* (2006.01)

(52) U.S. Cl.
CPC .......... *G01N 33/1846* (2013.01); *G01N 27/30* (2013.01); *G01N 27/308* (2013.01); *G01N 27/4166* (2013.01)

(58) Field of Classification Search
CPC ............... G01N 33/1846; G01N 27/30; G01N 27/4166; G01N 27/308
See application file for complete search history.

(56) References Cited

U.S. PATENT DOCUMENTS 4,169,902 A * 10/1979 De Long .............. C05G 3/0064
427/136
4,626,413 A * 12/1986 Blades ................... G01N 27/06
422/78

(Continued)

FOREIGN PATENT DOCUMENTS

DE 10 2008 010 581 A1 8/2009
WO 03/104765 A2 12/2003

*Primary Examiner* — J. Christopher Ball
(74) *Attorney, Agent, or Firm* — Maschoff Brennan

(57) ABSTRACT

The invention relates to an electrochemical method for determining the DOC and/or TOC and/or IC content in a water sample by means of anodic oxidation on electrodes in a closed electrolysis cell, wherein the carbon is oxidized at least partially to carbon dioxide ($CO_2$).
The carbon dioxide thereby formed is collected in a closed gas space, wherein, in the range of the essentially linear increase in the $CO_2$ content in the gas space, the rate at which this increase takes place is determined and used in an analyzer unit to determine the DOC and/or TOC and/or IC content.

19 Claims, 2 Drawing Sheets

(56) References Cited

U.S. PATENT DOCUMENTS

Figure 4:
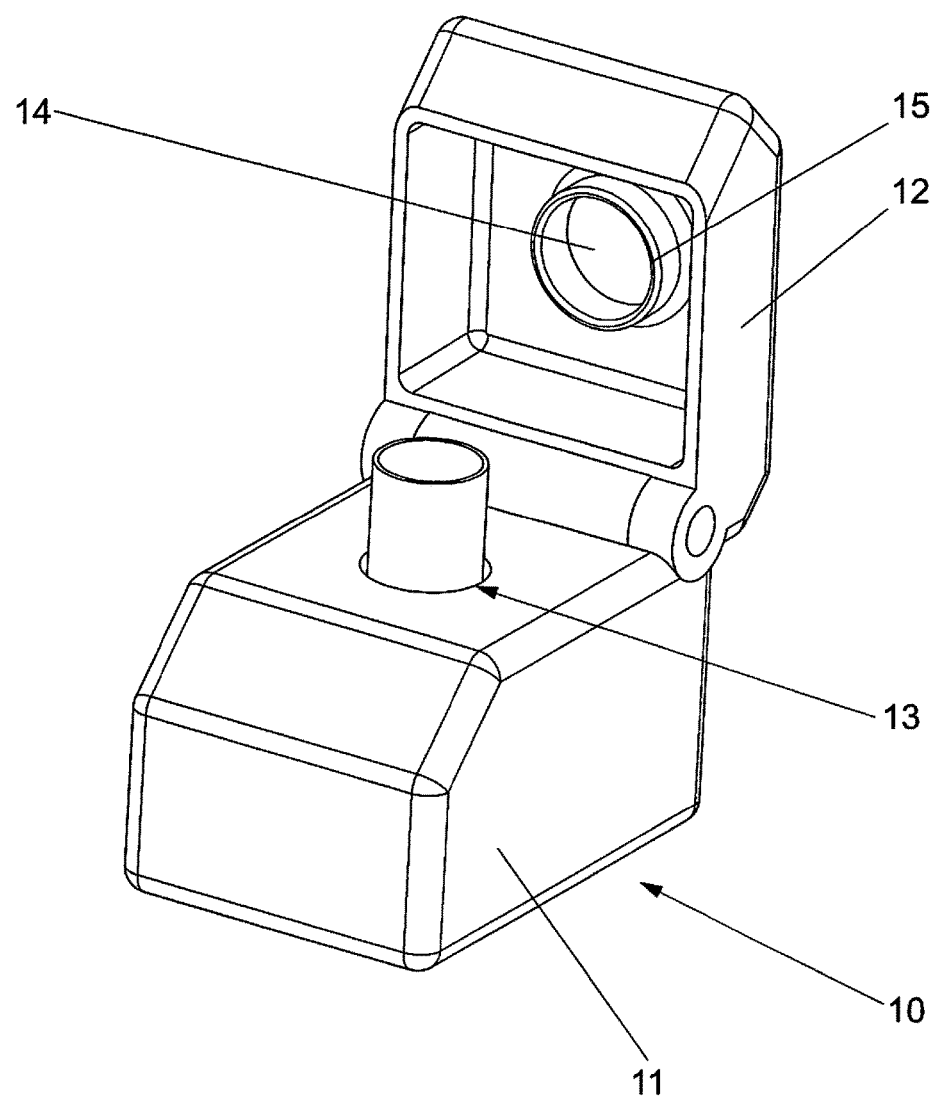

| | | | |
|---|---|---|---|
| 5,672,516 A | 9/1997 | Jeffers | |
| 6,444,474 B1 | 9/2002 | Thomas et al. | |
| 2005/0226774 A1* | 10/2005 | Kounaves | G01N 33/1846 422/80 |
| 2007/0183929 A1* | 8/2007 | Erickson | G01N 27/308 422/80 |

* cited by examiner

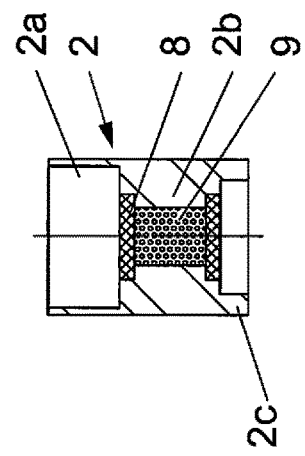
Fig. 3a Section III-III
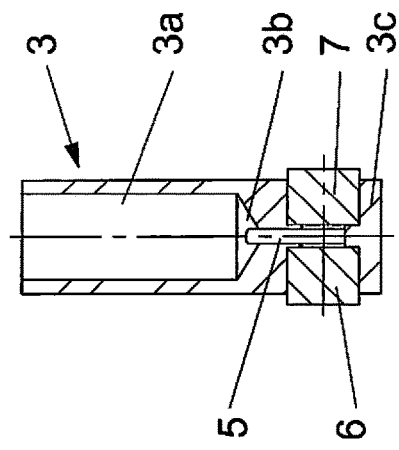
Fig. 3b Section III-III
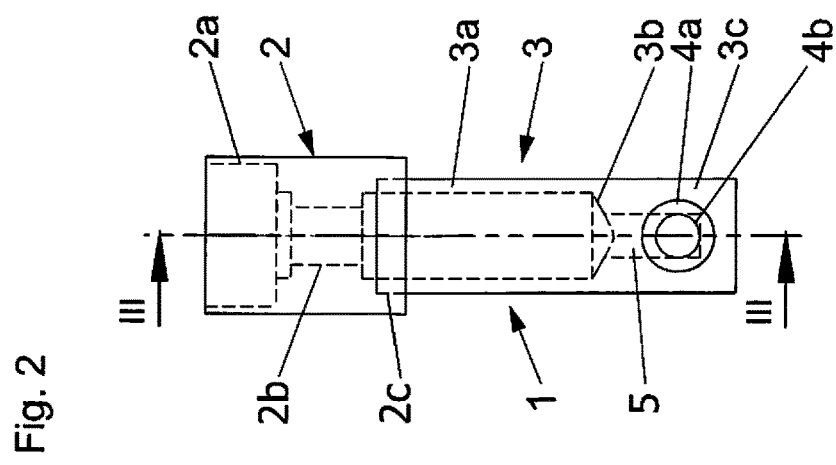
Fig. 2
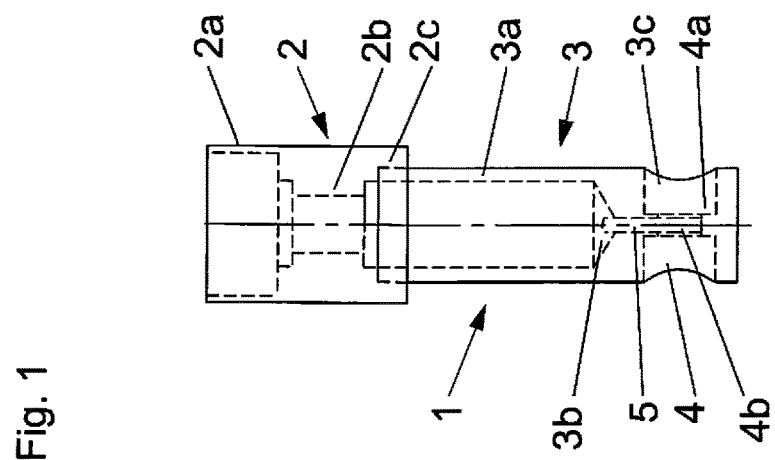
Fig. 1

ELECTROCHEMICAL METHOD AND DEVICE FOR DETERMINING THE CONTENT OF DOC AND/OR TOC AND/OR IC IN AN AQUEOUS SAMPLE

The invention relates to an electrochemical method for determining the DOC and/or TOC and/or IC content in a water sample by means of anodic oxidation on electrodes in a closed electrolyte cell, wherein the carbon is at least partially oxidized to carbon dioxide. The invention also relates to a device for determining the DOC and/or TOC and/or IC content in a water sample by means of anodic oxidation on electrodes in a closed electrolyte cell, wherein at least one $CO_2$-selective sensor is provided for measuring the amount of $CO_2$ formed.

There is a high demand for measurements of the carbon parameter units DOC (Dissolved Organic Carbon), TOC (Total Organic Carbon) and IC (Inorganic Carbon) for analyzing the quality of water, for example, in water processing in sewage treatment plants, in monitoring industrial process waters and in monitoring outdoor areas, while, at the same time, corresponding analyses are disproportionately complicated to carry out in proportion to the analysis of other parameter units and are relatively expensive. The known traditional methods are based on incineration of the samples at high temperatures of 700° C. to 1000° C. on catalyst materials such as cerium oxide, in a stream of oxygen with subsequent detection of the $CO_2$ thereby formed by using suitable sensors, for example, IR detectors. Alternatively, devices with UV/persulfate digestion are also available. These methods require large quantities of oxygen because they work in a stream of oxygen, and most methods also require high reaction temperatures, which result in a high energy consumption by the analytical equipment. The state-of-the-art equipment using these methods is therefore hardly suitable for mobile use.

It is also known that organic substances dissolved in water can be oxidized to $CO_2$ by means of anodic oxidation on electrodes with a high excess voltage in comparison with the release of oxygen, for example, lead dioxide electrodes or boron-doped diamond electrodes. DE 10 2008 010 581 A1 discloses on this basis a TOC measuring unit, which utilizes electrolytic decomposition of water into $H_2$ and $O_2$ taking place as a side reaction during the complete decomposition of the organic substances as the source of a carrier gas stream, which transports the $CO_2$ thereby formed to the sensor. Therefore, this method does not require an external oxygen source but it does consume a great deal of electrical energy with a relatively long running time in order to maintain a continuous gas stream. In particular, high demands are also made of the sensor because only the $CO_2$ that has just been formed is measured in the gas stream.

The present invention is based on the object of making available a method and a device of the type defined in the introduction, which will permit a mobile and particularly user friendly measurement. The power consumption should be moderate and it should also be possible to cover it with commercial batteries and/or rechargeable batteries in addition to line power. The sample containers should facilitate handling even outdoors and should prevent contamination of water samples due to previous measurements. No chemicals requiring special disposal should be used. Short measurement times and minimum sample preparation should yield readily reproducible values. It should be possible to design the measurement device to be small, lightweight, but also sturdy and inexpensive at the same time.

With regard to the method, this object is achieved according to the invention by collecting the carbon dioxide formed on the anode in a closed gas space, wherein in the range of the essentially linear increase in $CO_2$ content in the gas space, the rate at which this increase takes place is determined and used in an analyzer unit to ascertain the DOC and/or TOC and/or IC content.

With regard to the device according to the invention, this object is achieved by providing separate sample containers and an external measuring unit, wherein a sample container can be inserted into the measuring unit and wherein the external measuring unit is provided with the $CO_2$ sensor, which can be positioned on the sample container to form or participate in forming a closed gas space in the sample container. An embodiment of the sample container having a top part and a bottom part containing the electrolysis cell is particularly advantageous.

Therefore, with the present invention, in contrast with DE 10 2008 010 581 A1, the $CO_2$ formed by electrolysis is collected in a closed cell, the gas space, during the measurement, so that the concentration of $CO_2$ there increases with an increase in the total pressure during the electrolysis in the gas space. The total amount of $CO_2$ released up to the respective point in time is therefore always measured. The method according to the invention makes use of the fact that the $CO_2$ content rises in a closed gas space, so that after an initial phase, there is an essentially linear increase in the $CO_2$ content, the "slope" of which is used to determine the DOC or TOC content. In the present invention, depending on the duration of electrolysis, higher partial pressures of the resulting $CO_2$ occur, so that, due to this process, a better precision can be achieved in the measurement while using sensors of the same quality. Therefore, this also simplifies the design of the measuring unit because no lines, openings or the like need be provided. The $CO_2$ present in the atmosphere might cause problems with an arrangement such as that disclosed in DE 10 2008 010 581 A1, in particular if the $CO_2$ were to reach the sensor via the outlet or if it were present in the air space above the water sample. With the known method, the measurement gas consists of the $CO_2$-free electrolysis gas plus the $CO_2$ that has just been formed, so that even small quantities of atmospheric $CO_2$ would lead to a major error. Therefore, not only would it be necessary to prevent $CO_2$ from diffusing out of the outlet, but also the reaction space and the line system would have to be purged of $CO_2$ prior to the measurement (flushing, binding, etc.). With the present invention, however, the initial value of the $CO_2$ concentration before starting the electrolysis can be measured and subtracted and/or the absolute value of the measurement is not needed due to the analysis of the increase in $CO_2$ concentration according to the invention.

The electrolysis cell is preferably operated at a voltage which is higher than the water decomposition voltage to also produce oxygen in addition to a high concentration of hydroxide radicals. This oxygen not only contributes toward more rapid formation of the $CO_2$ gas from the carbon compounds to be oxidized but also supports outgassing of the $CO_2$ thereby formed by forming bubbles. A typical voltage for the electrodes used here is more than 2 V, in particular more than 2.5 V.

As mentioned above, an important advantage of the present method is that it does not wait for complete oxidation of the total carbon in the water sample but instead the rate of the formation of carbon dioxide which correlates with the total concentration of dissolved carbon in the sample is used. This permits very short analysis times and a low energy consumption. Only a comparatively small amount of gas is formed in the short electrolysis time and this small amount is collected in the gas space with a moderate increase in pressure.

With the device according to the invention, the sample containers are not components of the measuring unit but instead are separate from it. They may be filled with the liquid sample and are readily stored in the meantime. The measurement with one embodiment of the sample container having a top part and a bottom part is particularly convenient because with this embodiment, the liquid sample can be introduced into the bottom part, and then the top part, which is part of the subsequent gas space, is placed on top. Electrical contacting of the electrodes is provided only at the point when it (what?) is positioned in or on the measuring unit and the $CO_2$ detector is also accommodated in the measuring unit. Both the sample container and the measuring unit can be produced in a very compact and therefore mobile and inexpensive embodiment.

According to the invention it is also provided that the $CO_2$ formed in the electrolysis cell passes through a desiccant, in particular a molecular sieve, before reaching the gas space. This measure ensures that only $CO_2$ collects in the gas space but no moisture from the water sample reaches the gas space.

To determine the TOC content of a water sample, the carbon compounds present in a sparingly oxidizable form in the water sample are converted into dissolved carbon before the sample is introduced into the electrolysis cell. This conversion can be carried out easily by using the appropriate digestion chemicals such as acids, bases or hydrogenating substances depending on the nature and origin of the water sample.

Alternatively, by filtering the water sample before introducing it into the electrolysis cell, particulate carbon compounds can be removed from the water sample.

Furthermore, the handling of sample containers is particularly convenient when the bottom part is designed as an elongated body, for example, a hollow cylindrical body which is open at the top and is provided with openings at the side into which the electrodes are inserted from the outside with a seal, and on which the top part is also designed as an elongated body, for example, a cylindrical body, which can be placed on the bottom part and which encloses, in its top portion, a space that is open at the top and forms or participates in forming the case space in the measuring unit. It is particularly advantageous that such sample containers may be made of plastic and can be provided for a single use. The electrodes are designed in particular as small disks, which can be inserted more or less into the openings provided for this purpose on the bottom part from the outside with a seal. In this way, the electrodes can also be contacted in the measuring unit with no problem.

The measuring unit may advantageously be designed so that the $CO_2$ sensor is mounted on a part which is mounted movably on the measuring unit and which can be positioned with the sample container on the opening in the top part, so that the sensor also encloses the gas space, sealing it tightly. In a preferred embodiment of the invention, the $CO_2$ sensor is positioned on the inside of a cover that is hinged to the measuring unit.

The measuring unit may contain the control unit required for the measurement and preferably also the analyzer unit required for the analysis. Alternatively, it is possible to provide for the measured data to be transmitted from the measuring unit to an external device such as a cell phone, a tablet PC or the like. The control of the measurement and the analysis of the measurement results may take place on or from the external device.

To determine the IC content of a water sample, a special anode may be used in the sample container, namely an anode with a very low overvoltage in comparison with the release of oxygen, for example, made of copper and/or silver, so that this anode causes the release of gas without DOC oxidation in a phosphoric acid solution. The phosphoric acid solution may be introduced, for example, through introduction of phosphorus pentoxide powder into the water sample in the sample container has already been closed and inserted into the measuring unit. In an alternative embodiment, the anode of the electrolysis cell may also have an exterior layer or film made of a metal that dissolves under an anodic current flow, such as copper and/or silver as already mentioned, wherein phosphoric acid or a solid that forms phosphoric acid such as phosphorus pentoxide is added to a small cavity or reservoir behind this layer. This substance is released after the exterior layer dissolves so that the sample is acidified. This acidification releases the carbon dioxide which is bound inorganically, so that the carbon dioxide then enters the gas space where the increase in carbon dioxide is determined according to the invention.

In another advantageous embodiment of the invention, the anode is designed with multiple layers and has a diamond electrode or a lead dioxide electrode as the base layer and an outer copper layer and/or silver layer and a reservoir containing phosphoric acid or a phosphoric acid-forming solid. A two-step analysis is possible with an anode designed in this way, namely first the measurement of the IC and then measurement of the DOC/TOC in one analytical process. After dissolving the copper layer and/or silver layer, the diamond electrode and/or lead dioxide electrode behind it starts oxidizing the organic compound at a high excess voltage. In the first phase of analysis, the $CO_2$ thereby released can be attributed to the inorganic carbon whereas in the second phase it is attributed to the DOC and/or TOC.

The device according to the invention may also be designed in such a way that the sample container and the measuring unit are parts of a measuring system with an automated measurement system which operates continuously and includes in particular an automatic sampling system, automatic filling of the samples into the bottom parts in an autosampler, automatic positioning of the top parts and automatic placement in the measuring unit.

In another embodiment of the measuring unit according to the invention, at least one ultrasonic probe is installed beneath or at the side of the receptacle for the sample container in the measuring unit so that ultrasound can support the discharge of the $CO_2$ that is formed.

Additional features, advantages and details of the invention will now be described in greater detail on the basis of the drawings, which illustrate an exemplary embodiment, and in which FIG. 1 and FIG. 2 show side views of a sample container according to the invention, FIG. 3a and FIG. 3b each show a longitudinal section through the two main parts of the sample container according to sectional line III-III in FIG. 2, and FIG. 4 shows a view of a measuring unit.

In the following description of the figures, terms such as "top," "bottom," "vertical," "horizontal" and the like are referring to the positions of the respective parts of the sample container and/or the measuring unit illustrated in the figures.

FIGS. 1, 2, 3a and 3b illustrate one embodiment of a sample container 1 according to the invention. The sample container 1 consists of a top part 2 and a bottom part 3, such that the top part 2 can be attached to and/or pushed onto the bottom part 3 with a seal. The bottom part 3 is an essentially cylindrical body which has in particular a height of a few centimeter units, for example, on the order of 4 cm to 6 cm, and a maximum diameter unit of 10 mm to 25 mm, in particular on the order of 15 mm, and is open at the top and provided with a bottom. The bottom part 3 has a top cylindrical portion 3a which develops via a conical constriction 3b into a bottom portion 3c which is made of solid material, except for a horizontal borehole 4 and a central connecting channel 5 that runs vertically with an essentially oval or elongated hole-shaped cross section. The connecting channel 5 connects the borehole 4 to the cavity in the top portion 3a. In the embodiment shown here, the borehole 4 also has exterior borehole portions 4a on the bottom part 3 opening to the outside and having a slightly larger diameter unit than the short central borehole portions 4b which open into the connecting channel 5. As shown in FIG. 3a electrodes 6, 7 which in the embodiment shown here are designed in the form of disks held in the borehole portion 4a by a press fit or by means of an adhesive or inserted into the outer borehole portions 4a from the outside. The anodes may be lead dioxide electrodes or other electrodes having a high overvoltage with respect to oxygen production, but they are preferably diamond electrodes. Diamond film electrodes or solid diamond electrodes are preferred in particular, the latter also belonging to those having solid diamond particles embedded in a carrier material. The conductivity of the diamonds is ensured by doping, in particular with boron. In the case of diamond electrodes having a carrier material, this material may consist of plastic, titanium, graphite, lead and the like. The cathode may be a metallic electrode or a diamond electrode may also be used. The electrodes 6, 7 inserted into the borehole portions 4a can be contacted well electrically from the outside. The bottom part 3 of the sample body 1 thus forms an electrolysis cell.

The top part 2 is also a preferably cylindrical body, which has a hollow cylindrical top portion 2a, which makes available a gas space for collecting the $CO_2$ formed in the electrolysis cell, as will be described further below. This gas space in particular has a volume of 1 $cm^3$ to 20 $cm^3$. The top part which preferably has a height of 20 mm to 50 mm and an outside diameter unit of 14 mm to 30 mm also has a relatively short bottom portion 2c whose inside diameter unit is adapted to the outside diameter unit of the bottom part 3 in such a way that the top part 2 can be placed on the bottom part 3 with a slight press fit. In addition, a ring gasket may also be applied to the top part or bottom part, for example, a silicone gasket. Between the top portion 2a and the bottom portion 2c, there is a central portion 2b, in which, in the embodiment shown here, the top part 2 has a greater wall thickness than it does in the top portion and bottom portion 2a, 2c and which is delineated with respect to the top portion 2a and the bottom portion 2c by an element 8, which is permeable for gas but is largely impermeable for liquids, in particular a membrane and/or a gas-permeable mesh. Between the two elements 8, a desiccant is introduced in the form of granules and/or a powder 9, for example, calcium fluoride, phosphorus pentoxide or a zeolite molecular sieve. The gas space formed in the top portion 2a is open at the top as long as no measurement is taking place. The top part 2 and the bottom part 3 are made of plastic, except for the constituents inserted into them. The sample container 1 is preferably provided for a single use and is discarded after the measurement has been performed and/or some components thereof may be sent for recycling, if such is possible.

FIG. 4 shows schematically an embodiment of a measuring unit 10 which may also serve at the same time as an analyzer unit. The measuring unit 10 has a base part 11 and a cover 12 which is preferably arranged so that it can rotatably moved on the base part 11. A receptacle 13 for the sample container 1 is built into the base part 11, and the sample container 1 can be inserted from above vertically into the receptacle, which also ensures electrical contacting of the electrodes 6, 7 in the interior of the measuring unit. At least one $CO_2$ sensor 14, for example, an IR detector, is installed on the inside of the cover in such a way that, when the cover 12 is closed, a closure element 15 which encloses the sensor area, for example, in the form of a ring, ensures airtight closure of the gas space in the top portion 2a of the top part 2 of the inserted sample container 1.

A controller and analyzer unit together with the display of the measurement results can be integrated into the measuring unit 10. Alternatively, it is possible to provide that the measuring unit 10 is connected to a cell phone, a tablet PC or some other PC via Bluetooth, WLAN or the like, so that analysis and display of the measurement results on the respective external device are possible using special application software (an.

At least one ultrasonic probe which is not shown here but is available commercially can be installed in the measuring unit 10 beneath or at the side of the receptacle 13 for the sample container 1, supplying the electrical power in the base part 11.

To determine the DOC (dissolved organic carbon) content of a water sample, for example, wastewater, water from rivers or lakes, drinking water, bath water, groundwater and the like, a liquid sample is taken and optionally subjected to a sample preparation, for example, by filtration. The liquid sample is then introduced into the bottom part 3 which is positioned upright, of the sample container 1 and then the top part 2 is put in place. The sample container 1 can then be stored in an upright position for a long period of time. To carry out the measurement the sample container 1 is inserted into the receptacle 13 of the measuring unit 10 and the cover 12 is closed. By operating a switch or by deployment via the control software, even from an external device, operation of the electrolysis cell is started, i.e., electrodes 6, 7 are supplied with voltage. This voltage must be selected as a function of the cell geometry, the conductivity of the sample and the overvoltage of the electrodes so that electrolytic formation of oxygen/hydrogen can be observed. The power supply is therefore preferably regulated by regulating the amperage. The amperage can be kept constant but for special applications, the oxidation power can be varied by using different amperages on the electrodes. This procedure makes it possible to differentiate readily oxidizable TOC compounds from those that are difficult to oxidize. The amperage determines and/or influences the duration of the electrolysis and enters into the analysis of the measurement as a parameter unit. The organic carbon dissolved in the liquid sample is oxidized at least in part to $CO_2$ by means of anodic oxidation, so that the $CO_2$ rises into the closed gas space in the top part 2. The release of the $CO_2$ thereby formed can be supported by the ultrasound emitted by the ultrasonic probe. The operation of the ultrasonic probe can be started separately or automatically.

After a period of time, in particular a few minutes, after starting operation at a constant amperage, there is an almost linear increase in the $CO_2$ content in the gas space. It has been ascertained experimentally that the rate at which this increase takes place correlates with the total concentration of organic carbon in the water sample. The actual carbon content can therefore be derived, i.e., calculated, from the rate at which the $CO_2$ concentration has a linear increase by comparison with data (increase in the $CO_2$ content in the gas space over time) determined with samples with a known carbon content. This "comparison" is performed in the software of the analyzer unit.

Therefore, it is not necessary to wait for complete oxidation of the organic carbon in the sample as is the case with traditional DOC measuring units. This permits short analysis times, small electrode areas and a low energy consumption. Therefore, only a short electrolysis time is necessary and a comparatively small amount of electrolysis gas, which collects in the gas space with a moderate increase in pressure is formed. Fundamentally larger quantities of sample can therefore be used than is the case with the traditional methods, which thus facilitates representative sampling and measurement.

For special questions and/or for verifying whether the increase actually correlates with the total content with certain samples, it is possible to record and analyze complete oxidation of the sample by using the components of the device according to the invention, possibly with an increase in the size of the gas space, for example, through appropriate design of the top part or by reducing the amount of sample to enlarge the measurement area.

To also perform a measurement of the TOC (total organic carbon), i.e., a measurement which also includes the particulate carbon content in a water sample, the particulate carbon in the sample is converted to dissolved carbon in advance in the method according to the present invention. Depending on the nature and origin of the water sample, this conversion may take place through acidic, basic or hydrogenating digestion using non-oxidative chemicals, optionally with an increase in pressure, with an increase in temperature or with the use of catalysts. Next the water sample can be measured, as already described. This procedure has proven to be more reproducible and reliable than the conventional oxidative digestion in UV methods which can be carried out with only a low level of reproducibility, especially with particulate substances such as biopolymers and plastic particles. Digestion of the water sample therefore takes place in particular outside of the sample container and also outside of the measuring unit and therefore opens the possibility of converting even difficult-to-digest substances into dissolved carbon.

To optionally also be able to determine the IC content of a water sample. It is possible to provide for one anode to be used in sample container 1 with a very low overvoltage in comparison with the release of oxygen, in particular from copper and/or silver, which cause an evolution of gas in a phosphoric acid solution without oxidation of DOC. In the case of the closed sample container 1, for example, the phosphoric acid solution can be introduced by injecting phosphoric acid ($H_3PO_4$) into the water sample. Alternatively, the anode of the electrolysis cell may have an exterior layer made of a metal that dissolves under an anodic current flow, such as copper or silver, for example, in which case phosphoric acid or a solid that forms phosphoric acid, for example, phosphorus pentoxide, is placed in a cavity, i.e., reservoir, behind the layer, so that this substance is released after the layer dissolves and then the sample is acidified. Due to this acidification, the carbon dioxide bound at the anode is released into the gas space where the equivalent increase in carbon dioxide is detected. In another embodiment of the invention, the anode may be constructed of multiple layers, with a diamond electrode or a lead dioxide electrode as the base layer and a copper layer and/or silver layer and a reservoir with phosphoric acid or a solid that forms phosphoric acid. Such an anode permits a two-step analysis, first the measurement of the IC and then the measurement of the DOC/TOC in one analytical procedure. Only after the copper and/or silver layer(s) has/have dissolved does the diamond electrode or lead dioxide electrode behind it begin to oxidize the organic compounds at a great overvoltage. The $CO_2$ released in the first phase of the analysis can therefore be attributed to the inorganic carbon. The attribution to IC absolute values takes place like the attribution of the DOC values through "comparison" with suitable standard solutions in the form of calibration lines or calibration curves, as is customary in the state-of-the-art methods.

This sample container 1 may also be part of a continuous measurement system, in which the samples are taken by an automatic sampling system and placed in bottom parts 3 in an autosampler. The top parts 2 are put in position in a process that is just as automatic as is the positioning of the sample container 1 in the measuring unit 10.

The present invention is not restricted to the exemplary embodiment presented here. For example, it is possible to design the sample body in a form differing from the cylindrical form, for example, in a cubical form.

LIST OF REFERENCE NUMERALS

1 . . . sample container
2 . . . top part
2a . . . top portion
2b . . . middle portion
2c . . . bottom portion
3 . . . bottom part
3a . . . top portion
3b . . . constriction
3c . . . bottom portion
4 . . . borehole
4a . . . borehole portion
4b . . . central borehole portion
5 . . . connecting channel
6, 7 . . . electrodes
8 . . . membrane or mesh
9 . . . molecular sieve
10 . . . analyzer unit
11 . . . base part
12 . . . cover
13 . . . receptacle
14 . . . sensor
15 . . . ring-shaped closure element

The invention claimed is:
1. An electrochemical method for determining the DOC and/or TOC and/or IC content in a water sample by means of anodic oxidation on electrodes in a closed electrolysis cell, comprising:
  at least partially oxidizing carbon to carbon dioxide ($CO_2$),
    collecting the carbon dioxide thereby formed in a closed gas space during a range of an essentially linear increase in the carbon dioxide content in the closed gas space, and
    determining a rate that carbon dioxide content increases while the carbon dioxide content increase is in the range of the essentially linear increase in the carbon dioxide content in the closed gas space, and determining the DOC and/or TOC and/or IC content in the water sample with an analyzer unit based on the determined rate of carbon dioxide increase.

2. The method according to claim 1, wherein an anode with an overvoltage with respect to the formation of oxygen is used as the anode in the electrolysis cell the anode including a doped diamond electrode or a lead dioxide electrode, and wherein the potential of the overvoltage is exceeded during operation so that gaseous oxygen is formed in addition to OH radicals.

3. The method according to claim 1, wherein the $CO_2$ formed in the electrolysis cell passed through a desiccant upstream from the gas space.

4. The method according to claim 1, wherein particulate carbon compounds that are present in a sparingly oxidizable form are converted into dissolved carbon in the water sample before being introduced into the electrolysis cell by means of digestion chemicals.

5. The method according to claim 1, wherein the water sample is filtered before being introduced into the electrolysis cell.

6. A device for determining the DOC and/or TOC and/or IC content of a water sample by means of anodic oxidation on electrodes in a closed electrolysis cell, comprising:
   at least one $CO_2$ sensor used to measure the $CO_2$ thereby formed, and
   separate sample containers and an external measuring unit, wherein a sample container can be inserted into the measuring unit, and wherein the external measuring unit is provided with the $CO_2$ sensor, which can be positioned on the sample container to form or participate in forming a closed gas space in the sample container,
   wherein the $CO_2$ sensor is positioned on the inside of an element which is hinged to the measuring unit.

7. The device according to claim 6, wherein the sample container has a top part and a bottom part which contain the electrolysis cell.

8. The device according to claim 7, wherein the bottom part is designed as an elongated body which is open at the top and is provided with openings at the sides into which the electrodes are inserted from the outside with a seal.

9. The device according to claim 7, wherein the top part is designed as an elongated body which can be placed on the bottom part and which contains a space that is open at the top in its top portion, which thus forms the gas space.

10. The device according to claim 7, wherein a desiccant is contained in the top part beneath the space that is open at the top.

11. The device according to claim 10, wherein the desiccant is provided between two membranes and/or meshes which are permeable for gas but are largely impermeable for liquid.

12. The device according to claim 7, wherein the sample container and the measuring unit are parts of a measuring system, which operates an automated measuring system continuously, having an automatic sampling system, an automatic system for filling the samples into the bottom parts, which are in an autosampler, automatic placement of the top parts and automatic positioning in the measuring unit.

13. The device according to claim 6, wherein the measuring unit is a control unit which contains an analyzer unit.

14. The device according to claim 6, wherein the measured data can be retrieved from the measuring unit to an external device and can be stored on this device and processed further there.

15. The device according to claim 14, wherein the control of the measurement and the analysis of the measurement results take place from and/or on the external device.

16. The device according to claim 6, wherein an anode having a very slight overvoltage in comparison with the release of oxygen is used in the sample container, causing the release of gas without oxidation of DOC in a phosphoric acid solution.

17. A device for determining the DOC and/or TOC and/or IC content of a water sample by means of anodic oxidation on electrodes in a closed electrolysis cell, comprising:
   at least one $CO_2$ sensor used to measure the $CO_2$ thereby formed, and
   separate sample containers and an external measuring unit, wherein a sample container can be inserted into the measuring unit, and wherein the external measuring unit is provided with the $CO_2$ sensor, which can be positioned on the sample container to form or participate in forming a closed gas space in the sample container, wherein the anode in the sample container has an exterior layer, which is a copper and/or silver electrode, wherein there is a reservoir containing a substance that forms phosphoric acid behind this layer.

18. The device according to claim 17, wherein the anode behind the reservoir has a layer of a diamond electrode or a lead dioxide electrode.

19. A device for determining the DOC and/or TOC and/or IC content of a water sample by means of anodic oxidation on electrodes in a closed electrolysis cell, comprising:
   at least one $CO_2$ sensor used to measure the $CO_2$ thereby formed, and
   separate sample containers and an external measuring unit, wherein a sample container can be inserted into the measuring unit, and wherein the external measuring unit is provided with the $CO_2$ sensor, which can be positioned on the sample container to form or participate in forming a closed gas space in the sample container, wherein at least one ultrasonic probe is installed beneath or at the side of the receptacle for the sample container in the measuring unit.

* * * * *